Figure 1:
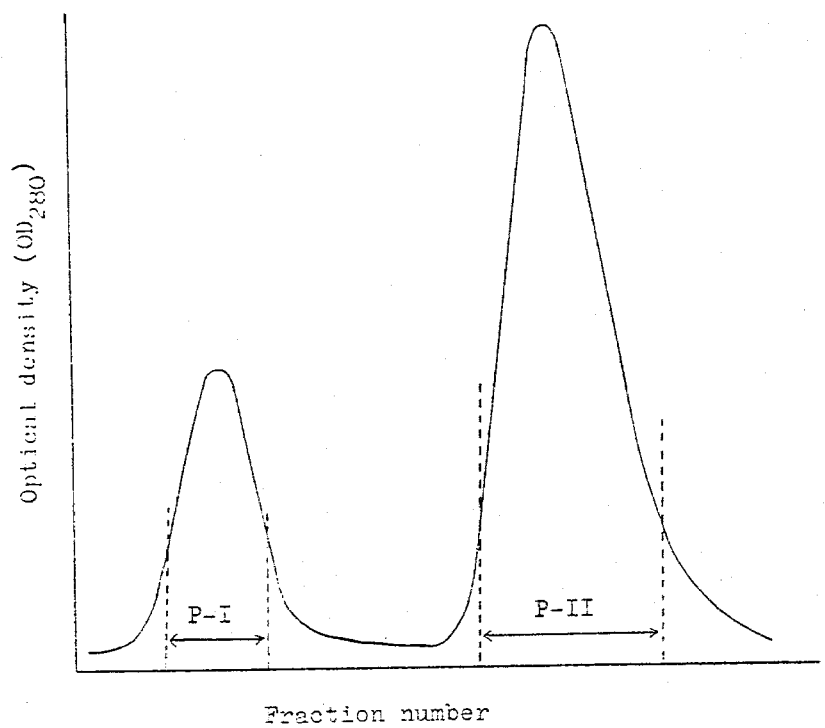

United States Patent [19]

Funatsu et al.

[11] 4,302,384
[45] Nov. 24, 1981

[54] PURIFICATION OF GAMMAGLOBULIN DERIVATIVE

[75] Inventors: Akinobu Funatsu; Shuzoh Oyama; Yoshinori Akimoto; Komei Ohashi, all of Kumamoto, Japan

[73] Assignee: Juridical Foundation, The Chemo-Sero-Therapeutic Research Institute, Kumamoto, Japan

[21] Appl. No.: 98,789

[22] Filed: Nov. 30, 1979

[30] Foreign Application Priority Data

Jan. 17, 1979 [JP] Japan ................................ 54-4177

[51] Int. Cl.³ ........................ C07G 7/00; A61K 39/00
[52] U.S. Cl. .................................. 260/112 B; 424/85
[58] Field of Search ...................... 260/112 B, 112 R; 424/85

[56] References Cited

U.S. PATENT DOCUMENTS 3,869,436 3/1975 Falksveden ................ 260/112 B
4,059,571 11/1977 Tomibe et al. ............. 260/112 B
4,100,149 7/1978 Meiller et al. ............. 260/112 B

OTHER PUBLICATIONS

Habeeb et al., Vox Sang., vol. 31, pp. 423-434 (1976).
Habeeb et al., Vox Sang., vol. 32, pp. 143-158 (1977).
Chemical Abstracts, vol. 86, Abstract No. 104271f, Masuho et al., "Development of an Intravenous γ-6l," 1977.

Primary Examiner—Delbert R. Phillips
Assistant Examiner—Blondel Hazel
Attorney, Agent, or Firm—Stevens, Davis, Miller & Mosher

[57] ABSTRACT

Process for the production of a highly purified S-sulfonated gammaglobulin by treating an S-sulfonated gammaglobulin obtained by sulfonating a conventional gammaglobulin with an ion exchanger in a buffer solution for development, and thereby absorbing single molecular S-sulfonated gammaglobulin thereto, and eluting the single molecular S-sulfonated gammaglobulin with a buffer solution for elution. This process can give the desired S-sulfonated gammaglobulin having a high content of single molecule and an extremely small anticomplementary activity (e.g. $CH_{50}$ of 10% or less) and also an excellent shaking stability from the conventional gammaglobulin in an industrial scale.

9 Claims, 2 Drawing Figures

PURIFICATION OF GAMMAGLOBULIN DERIVATIVE

The present invention relates to a method for purification of gammaglobulin. More particularly, it relates to a method for production of purified, S-sulfonated gammaglobulin comprising treating S-sulfonated gammaglobulin with an ion exchanger, by which agglutinated molecules of the S-sulfonated gammaglobulin are sufficiently removed to increase of content of the single molecular compound and the undesirable anticomplementary activity is sufficiently decreased to give the desired, biologically and physically stable S-sulfonated gammaglobulin.

It is well known that gammaglobulin fractionated from blood plasma mixture has antibody activities against various infectious diseases and is useful as so-called immunoglobulin preparation for the prophylactic and therapeutic treatment of various infectious diseases. However, the conventional immunoglobulin preparation contains agglutinated molecules which are produced during the step of purification thereof, and hence, it can not be administered in an intravenous route and can only be administered in intramuscular route. It is also known that when a gammaglobulin preparation containing a large amount of agglutinated molecules is intravenously administered to a patient, a complement is rapidly activated in the patient, which induces various side effects such as lowering of blood pressure, increase of body temperature, disorders of circulation system, or the like. On the other hand, when the gammaglobulin is administrated in intramucular route, the administration amount and the penetration rate of gammaglobulin into blood vessel are limited, and hence, the intramuscular administration is not suitable when rapid increase of blood level of the antibody is required. Accordingly, it has been required to find an improved gammaglobulin which can intravenously be administered without trouble due to anticomplementary activity.

There have been proposed various methods for the preparation of intravenously administrable gammaglobulin, for example, a method of treatment with pepsin [cf. H. E. Schultze; Deutsch Medizinishe Wochemshrift, Vol. 87, page 1643 (1962)], and a method of the treatment with plasmin [cf. J. T. Sgouris; Vox Sanguinis, Vol. 13, page 71 (1967)]. However, according to the method of the treatment with a protease such as pepsin, the gammaglobulin is decomposed into two or more lower molecular compounds, and hence, the produced antibody disappears within a shorter period of time and further the biological activity of Fc moeity of gammaglobulin molecule is decreased due to cutting off of the Fc moiety.

It has also been proposed to give an intravenously administrable gammaglobulin without the above drawbacks, i.e. to provide the desired gammaglobulin without substantially changing the structure of gammaglobulin, for example a method of the treatment of gammaglobulin at pH 4 [cf. S. Barundun et al; Vox Sanguinis, Vol. 13, page 93 (1976)], and a method of the treatment with β-propiolactone [cf. W. Stephan; Vox Sanguinis, Vol. 28, page 422 (1975)]. According to the method of the treatment at pH 4, however, content of agglutinated molecules is increased during the storage of the gammaglobulin thus obtained and it tends to again increase the anticomplementary activity. Besides, they say that the gammaglobulin produced by the treatment with β-propiolactone might be possible to function as an antigen when administered.

It has recently been reported by Masuho et al that a suitable, intravenously administrable gammaglobulin can be produced by sulfonation of S-S chain of gammaglobulin (cf. U.S. Pat. No. 4,059,571, Japanese Patent Publication (unexamined) No. 1630/1976). The S-sulfonated gammaglobulin produced by Masuho et al retains the original high molecule owing to hydrogen bonding while the S-S bond is broken and hence, it shows remarkably decreased anticomplementary activity with retaining completely the antibody activity (they say that the anticomplementary activity level at a concentration of proteins of 5% by weight (hereinafter, referred to as "$CH_{50}$") is 30% or less), and further, the S-sulfonated gammaglobulin is readily reduced and then oxidized to produce the original gammaglobulin when administered to human body [cf. Masuho et al, Journal of Biochemistry, Vol. 19, page 1377 (1976)]. It was also proved that the S-sulfonated gammaglobulin can stably be administered to low gammaglobulinemic or agammaglobulinemic subjects by clinical tests (cf. Noboru Kobayashi; International Academy of Blood Transfusion (Paris), 1978).

Thus, the S-sulfonated gammaglobulin is excellent and useful as an intravenously administrable gammaglobulin preparation and attention is given thereto. However, this product has a drawback that it can hardly be produced in an industrial scale. That is, according to the process for the production thereof by Masuho et al as mentioned hereinbefore, when the starting gammaglobulin is sufficiently purified and has less agglutinated molecules, there can be obtained the desired S-sulfonated gammaglobulin having a low anticomplementary activity, but when the conventional gammaglobulin which is industrially used, for example, the gammaglobulin produced by Cohn's fractionation method using ethanol at a low temperature, is used as the starting material, the produced S-sulfonated gammaglobulin has an anticomplementary activity which is not so low (at lowest $CH_{50}$=about 30 to 20%). Thus, the process of Masuho et al is excellent in priciple, but it should be accompanied with any additional treatment in order to obtain the desired product having a high stability in an industrial scale.

Under the circumstance, the present inventors have intensively studied to find an improved process for the production of the desired S-sulfonated gammaglobulin having a sufficiently low anticomplementary activity even if any conventional gammaglobulin containing much agglutinated molecules is used as the starting material. As a result, it has now been found that after sulfonation reaction, the resulting S-sulfonated gammaglobulin is treated with an ion exchanger, and thereby, there can be obtained the desired S-sulfonated gammaglobulin having an extremely low anticomplementary activity.

An object of the present invention is to provide an improved process for the production of an intravenously administrable gammaglobulin in an industrial scale. Another object of the invention is to provide an S-sulfonated gammaglobulin which comprises predominantly a single molecule with less agglutinated molecules and has an extremely low anticomplementary activity. A further object of the invention is to provide a method for purification of an S-sulfonated gammaglobulin. These and other objects and advantages of the present invention will be apparent from the following description.

According to the present invention, the S-sulfonated gammaglobulin produced by sulfonating the conventional gammaglobulin by a known method is passed through an ion exchanger to separate into a fraction comprising premodinantly agglutinated molecules and a fraction comprising predominantly single molecular gammaglobulin, and the latter fraction is collected to give the desired S-sulfonated gammaglobulin having an extremely low anticomplementary activity. The single molecular S-sulfonated gammaglobulin obtained by the process of the present invention has a $CH_{50}$ of less than 10% and hence is suitable as an intravenously administrable immunoglobulin preparation.

The starting S-sulfonated gammaglobulin may be prepared by using a conventional gammaglobulin which is usually prepared by Cohn's fractionation method which has internationally widely been used for the preparation of gammaglobulin [cf. J. Am. Chem. Soc., Vol. 68, page 459 (1946)]. The gammaglobulin is sulfonated by treating with an oxidizing agent such as an alkali metal tetrathionate, an alkali metal iodosobenzoate, a molecular oxygen-containing gas (e.g. air) or a sulfite ion-generating compound (e.g. sulfurous acid) (cf. U.S. Pat. No. 4,059,571, Japanese Patent Publication (unexamined) Nos. 1630/1976 and 76418/1976). The S-sulfonated gammaglobulin may optionally be purified by a conventional method such as dialysis.

The ion exchanger used in the present invention is preferably a repeatedly usable column without specific activation and has a large binding capacity and is preferably an autoclavable gel having good stability under various conditions, e.g. at various pH levels, ionic strengths, etc.

The ion exchanger includes anion exchangers and cation exchangers, but anion exchangers are preferable from the viewpoint of the biological and physical stabilities of the product. The anion exchanger may be used in combination with the cation exchanger.

Suitable examples of the anion exchanger are agarose gel introduced with an anionic substituent (e.g. DEAE-Sepharose CL-6B), dextran gel introduced with an anionic substituent (e.g. DEAE-Sephadex, QAE-Sephadex), cellulose gel introduced with an anionic substituent (e.g. DEAE-cellulose, TEAE-sellulose), polyvinyl gel introduced with an anionic substituent (e.g. DEAE-TOYOPEAL), amylose gel introduced with an anionic substituent, or the like. The anionic substituent includes diethylaminoethyl (DEAE), triethylaminoethyl (TEAE) and diethyl-(2-hydroxypropyl)aminoethyl (QAE).

Suitable examples of the cation exchanger are agarose gel introduced with a cationic substituent (e.g. CM-Sepharose CL-6B), dextran gel introduced with a cationic substituent (e.g. CM-sephadex, SP-Sephadex), cellulose gel introduced with a cationic substituent (e.g. CM-cellulose), polyvinyl gel introduced with a cationic substituent (e.g. CM-TOYOPEAL), amylose gel introduced with a cationic substituent, or the like. The cationic substituent includes carboxymethyl (CM), sulfopropyl (SP) and sulfoethyl (SE).

The absorption of the S-sulfonated gammaglobulin onto an ion exchanger may be carried out as follows. The S-sulfonated gammaglobulin is treated with an ion exchanger in a buffer solution for development which has an optimum hydrogen ion level (pH level) and an optimum ionic strength, and thereby, the single molecular S-sulfonated gammaglobulin is absorbed onto the ion exchanger. By this treatment, the agglutinated molecules of S-sulfonated gammaglobulin and also un-sulfonated gammaglobulin pass through the ion exchanger without being absorbed thereto. After the absorption, the ion exchanger is washed with the same buffer solution in order to completely remove the agglutinated gammaglobulin and other impurities.

The buffer solution used for the absorption of the single molecular S-sulfonated gammaglobulin has pH level of 4 to 10, preferably 7 to 8, and an ionic strength ($\mu$) of 0.01 to 0.15, preferably 0.03 to 0.09, in case of anion exchanger. Besides, when a cation exchanger is used, the buffer solution has a pH level of 4 to 6.5, preferably 5 to 6, and an ionic strength of 0.01 to 0.1, preferably 0.035 to 0.07. Concentration of the S-sulfonated gammaglobulin to be subjected to the absorption treatment is not critical, but in view of the exchange capacity of the ion exchanger, the S-sulfonated gammaglobulin is preferably used in a concentration of 2 to 12 W/V %.

The buffer solution for development include a phosphate buffer solution, a citrate buffer solution, a Tris-phosphate buffer solution, a Tris-HCl buffer solution, a borate buffer sulution, an acetate buffer solution, or the like.

The single molecular S-sulfonated gammaglobulin absorbed onto the ion exchanger is easily recovered therefrom by eluting out with a buffer solution which has a pH level and ionic strength different from those of the buffer solution for development. The buffer solution for elution has a pH level of 3 to 4 in case of using an anion exchanger and a pH level of 6 to 9 in case of using a cation exchanger. The ionic strength ($\mu$) of the buffer solution for elution should be higher than that of the buffer solution for development and it is preferably in the range of 0.05 to 0.8. The buffer solution for elution includes a phosphate buffer solution, a glycine-HCl buffer solution, a citrate buffer solution, an aqueous solution of sodium acetate, or the like. These buffer solutions may contain sodium chloride.

The purification treatment of the present invention is usually carried out at room temperature, but may be done under cooling.

The S-sulfonated gammaglobulin purified by the present invention has a higher content of single molecule, a less anticomplementary activity and a greater stability in comparison with the product before purification. For instance, when the S-sulfonated gammaglobulin as used in Example 1 hereinafter (three lots) was purified according to the process of the present invention using DEAE-Sepharose CL-6B and CM-Sepharose CL-6B and the resulting product was regulated so as to become a protein concentration of 5%, the products showed such an anticomplementary activity ($CH_{50}$), content of single molecule (measured by a ultracentrifugal analysis) and shaking stability (measured by means of the difference of light-scattering after shaking with Kahn's shaking machine) as shown in Table 1.

TABLE 1

| | | | After purification | |
| | Lot No. | Before purification | Using DEAE-Sepharose | Using CM-Sepharose |
| --- | --- | --- | --- | --- |
| Anticomple-[*1] mentary activity ($CH_{50}$) (%) | i | 25 | 6 | 8 |
| | ii | 20 | 3 | 10 |
| | iii | 22 | 5 | 7 |

TABLE 1-continued

|  | Lot No. | Before purification | After purification Using DEAE-Sepharose | After purification Using CM-Sepharose |
|---|---|---|---|---|
| Content of*2 | i | 82 | 92 | 90 |
| single | ii | 84 | 92 | 92 |
| molecule |  |  |  |  |
| (%) | iii | 85 | 94 | 95 |
| Shaking*3 | i | 100 | 5 | 42 |
| stability | ii | 80 | 8 | 38 |
|  | iii | 136 | 2 | 30 |

[Remarks]:
*1It was measured according to Kabat Mayer process [cf. Experimental Immunochemistry page 225 (1961)].
*2It was measured after centrifugation at 60,000 rpm for 50 minutes with Beckmann ultra-centrifugal machine.
*3It was measured by shaking the product at an amplitude of 3.4 cm/sec. and 3.7 cycle/sec. for 4 hours, irradiating thereto a light and then measuring the difference of the light-scattering before and after the shaking (cf. Standard for Biological Preparations, editing by Ministry of Health and Welfare, Japan).

As is clear from the results as shown in Table 1, the S-sulfonated gammaglobulin purified by the present invention shows an extremely decreased anticomplementary activity, i.e. 10% or less at a protein concentration of 5%, in comparison with that of the product before purification. In case of using an anion exchanger, it is particularly extremely decreased. Content of single molecule is increased from 75 to 80% (before purification) to 90 to 95% (after purification). According to ultracentrifugal analysis, the largely agglutinated molecules are hardly analyzed, because they precipitate immediately after initiation of centrifugation, but according to gel chromatographic analysis (e.g. thin layer gel chromatography), the agglutinated molecules can be separated into polymers and oligomers. According to this gel chromatographicc analysis, it was confirmed that the content of monomer (single molecule) was increased from 60 to 70% (before purification) to 85% or more (after purification). Moreover, according to the measurement of light-scattering before and after purification, the S-sulfonated gammaglobulin purified by the present invention shows an extremely high stability and no insoluble substance precipitates even by shaking.

The present invention is illustrated by the following Examples, wherein % is % by weight unless specified otherwise.

EXAMPLE 1

Sodium tetrathionate (248 g) and sodium sulfite (408 g) were separately dissolved in sodium chloride-containing phosphate buffer solution (pH 7.6) (1,500 ml and 3,500 ml, respectively), followed by filtration in order to sterilization. Each solution thus prepared was added to a 15% aqueous solution of gammaglobulin (10 liters) which was prepared from human blood plasma by ethanol-fractionation method and the mixture was slowly stirred at 43° C. for 4.5 hours to proceed sulfonation.

After the reaction, the reaction mixture was dialyzed against a physiological saline solution in order to remove the excess sulfonating agent and then equilibrated with a buffer solution for development (a phosphate buffer solution; $\mu=0.06$, pH 7.5).

The solution of S-sulfonated gammaglobulin in phosphate buffer was regulated to become a protein concentration of about 8%, and the solution (15 liters) was developed by passing through a column (16 liters) packed with DEAE-Sepharose CL-6B (made by Pharmacia) which was equilibrated with the same phosphate buffer solution as used above. The fraction (P-I) which passed through the column without being absorbed onto the ion exchanger was a solution having a protein concentration of about 2% (16 liters).

The column was washed well with the same phosphate buffer solution as used above, and when protein was almost no more detected, an acetate buffer solution ($\mu=0.1$, pH 4.0) was passed through the column and the eluted fraction (P-II) was collected. Said fraction (P-II) was a solution having a protein concentration of about 2.5% (32 liters).

Each fraction obtained above was neutralized with an aqueous sodium hydroxide solution, concentrated until the protein concentration became about 5%, and then dialyzed against a 2.25% glycine-containing isotonic phosphate buffer solution. Various properties of the products thus obtained were measured in the same manner as shown in Table 1. The results are shown in Table 2.

TABLE 2

|  | Before purification | After purification P-I | After purification P-II |
|---|---|---|---|
| Anticomplementary activity (CH$_{50}$) (%) | 24 | 52 | 4 |
| Content of single molecule (%) | 82 | 50 | 94 |
| Shaking stability | 120 | 207 | 3 |

As is clear from the above results, the P-I fraction has a high anticomplementary activity and contains a large amount of agglutinated molecules and is inferior in the shaking stability. On the other hand, the desired P-II fraction has a sufficiently low anticomplementary activity, a high content of single molecule and an extremely increased shaking stability. Thus, the components having undesirable properties are effectively removed as the P-I fraction.

The separation pattern of the fractions in the above Example 1 is shown in the accompany FIG. 1, wherein the abscissa axis is the fraction number and the ordinate axis is the optical density of each fraction at a wave length of 280 nm.

Figure 2:
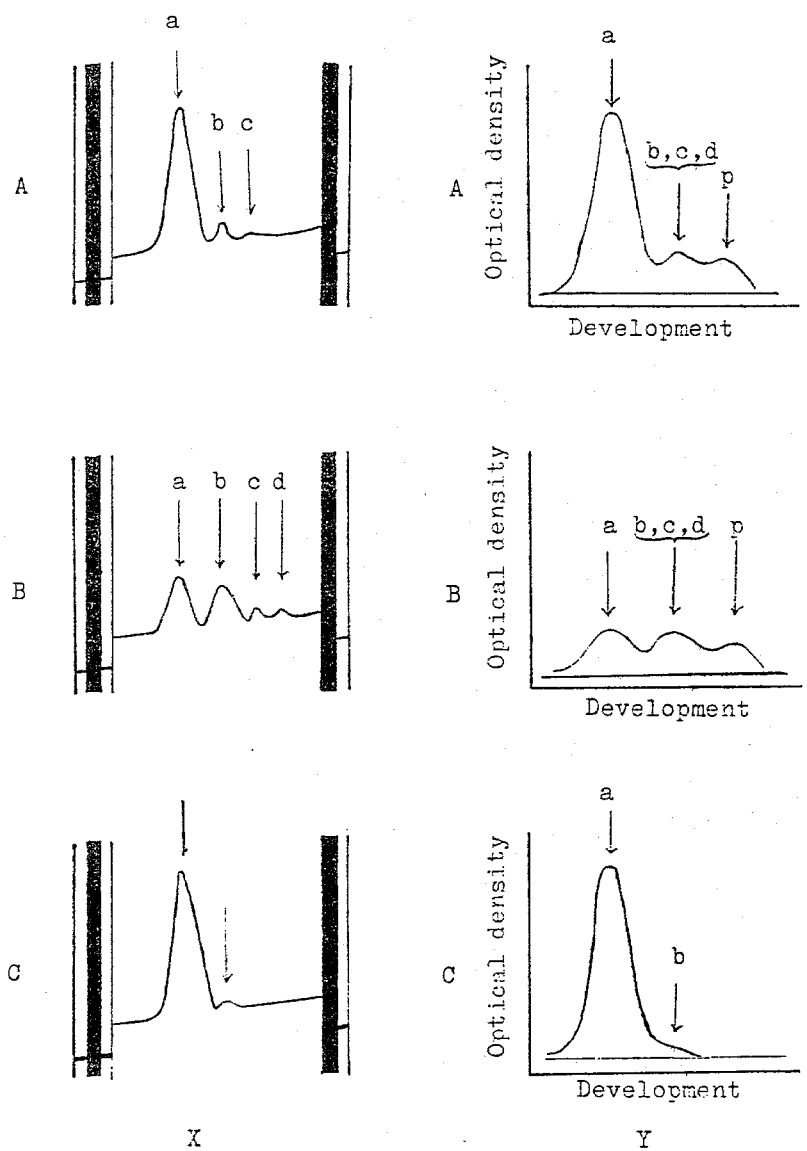

Besides, the solution of S-sulfonated gammaglobulin before purification (A), the P-I fraction (B) and the P-II fraction (C) were subjected to ultra-centrifugal analysis (X) and thin layer gel filtration analysis (Y). The patterns in these analyses are shown in the accompanying FIG. 2. The ultra-centrifugal analysis was carried out under the conditions of a protein concentration of about 1.67%, at 60,000 rpm for 50 minutes by using a Beckman ultra-centrifugal machine, and the thin layer gel filtration analysis was carried out in according with Migita's method [cf. Annual Report of Inst. Virus Research, Kyoto Univ., Vol. 8, page 130 (1965)]. In FIG. 2, "a" is a single molecular substance (7S), and "b", "c" and "d" are oligomers (9S, 11S and 13S, respectively), and "p" is a polymer. As is clear from FIG. 2, both analyses show similar pattern, but the amount of the largely agglutinated molecules appears higher in the thin layer gel filtration analysis than in the ultra-centrifugal analysis. In the pattern of the ultra-centrifugal analysis, the polymer does not appear. Both analyses show that the P-I fraction contains a large amount of agglutinated molecules and the P-II faction contains an increased amount of single molecule.

EXAMPLE 2

A 15% aqueous solution of gammaglobulin was sulfonated and followed by dialysis in the same manner as described in Example 1. The S-sulfonated gammaglobulin solution thus obtained was regulated so as to become a protein concentration of about 7%. The solution (about 100 liters) was passed through a column (150 liters) packed with DEAE-Sepharose CL-6B which was equilibrated with a citrate buffer solution ($\mu=0.03$, pH 7.5). The fraction (p-I) which passed through the column without being absorbed onto the ion exchanger was a solution having a protein concentration of about 1.5% (about 125 liters).

After washing the column in the same manner as described in Example 1, a sodium chloride-containing glycine-HCl buffer solution ($\mu=0.55$, pH 3.5) was passed through the column and the eluted fraction (P-II) was collected. Said fraction (P-II) was a solution having a protein concentration of about 2% (about 245 liters).

The fractions thus obtained were treated in the same manner as described in Example 1, and the various properties thereof were measured likewise. The results are shown in Table 3.

TABLE 3

|  | Before purification | After purification P-I | After purification P-II |
|---|---|---|---|
| Anticomplementary activity (CH$_{50}$) (%) | 25 | 58 | 5 |
| Content of single molecule (%) | 82 | 50 | 94 |
| Shaking stability | 137 | 238 | 3 |

EXAMPLE 3

In the same manner as described in Example 1 except that a citrate buffer solution ($\mu=0.03$, pH 7.5) was used instead of the phosphate buffer solution ($\mu=0.06$, pH 7.5) as the buffer solution for development, a solution (about 15 liters) of S-sulfonated gammaglobulin having a protein concentration of about 7% was developed by passing through a column (16 liters) which was packed with DEAE-Sepharose CL-6B. As a result, there was obtained P-I fraction (15.6 liters) having a protein concentration of about 1.7%. By using a citrate buffer solution ($\mu=0.614$, pH 6.0) as the buffer solution for elution, there was obtained P-II fraction (31 liters) having a protein concentration of about 2.2%.

EXAMPLE 4

The above Example 3 was repeated except that a phosphate buffer solution ($\mu=0.06$, pH 7.5) was used. As a result, there was obtained P-I fraction (about 14 liters) having a protein concentration of about 1.8%. Furthermore, by eluting with a glycine-HCl buffer solution ($\mu=0.542$, PH 3.5), there was obtained P-II fraction (29 liters) having a protein concentration of about 2.4%.

EXAMPLE 5

The above Example 3 was repeated except that a Tris-HCl buffer solution ($\mu=0.0175$, pH 8.5) was used as the buffer solution for development and a sodium chloride-containing phosphate buffer solution ($\mu=0.45$, pH 6.0) was used as the buffer solution for elution. As a result, there were obtained P-I fraction (22 liters) having a protein concentration of about 1.2% and P-II fraction (27 liters) having a protein concentration of about 2.6%.

EXAMPLE 6

An aqueous solution of S-sulfonated gammaglobulin prepared in the same manner as described in Example 1 was equilibrated by dialysis against an acetate buffer ($\mu=0.05$, pH 5.3). The solution was regulated so as to become a concentration of S-sulfonated gammaglobulin of about 7%, and the resulting solution (15 liters) was passed through a column (16 liters) packed with CM-Sepharose CL-6B (made by Pharmacia) which was equilibrated with the same acetate buffer solution as used above. The fraction (P-I) which passed through the column without being absorbed thereto was a solution having a protein concentration of about 1.9% (13 liters).

After washing the ion exchanger column in the same manner as described in Example 1, an aqueous solution of sodium acetate ($\mu=0.2$) was passed through the column and the eluted fraction (P-II) was collected. Said P-II fraction was a solution having a protein concentration of about 2.5% (27 liters).

Each fraction thus obtained was treated in the same manner as described in Example 1, and various properties thereof were measured likewise. The results are shown in Table 4.

TABLE 4

|  | Before purification | After purification P-I | After purification P-II |
|---|---|---|---|
| Anticomplementary activity (CH$_{50}$) (%) | 25 | 32 | 8 |
| Content of single molecule (%) | 83 | 48 | 95 |
| Shaking stability | 102 | 180 | 32 |

What is claimed is:

1. A process for the production of a purified S-sulfonated gammaglobulin which comprises treating an S-sulfonated gammaglobulin with an anion exchanger in a buffer solution for development having a pH level of 7 to 8 and an ionic strength of 0.01 to 0.15 and thereby absorbing single molecular S-sulfonated gammaglobulin on the anion exchanger, and then eluting the single molecular S-sulfonated gammaglobulin with a buffer solution for elution.

2. A process according to claim 1, wherein the anion exchanger is a member selected from the group consisting of agarose gel introduced with an anionic substituent, dextran gel introduced with an anionic substituent, cellulose gel introduced with an anionic substituent, polyvinyl gel introduced with an anionic substituent, and amylose gel introduced with an anionic substituent, said anionic substituent being a member selected from the group consisting of diethylaminoethyl, triethylaminoethyl and diethyl-(2-hydroxypropyl)aminoethyl.

3. A process according to claim 1 or 2 therefor, wherein a buffer solution having a pH level of 3 to 4 and an ionic strength of higher than that of the buffer solution for development is used as the buffer solution for elution.

4. A process according to claim 3, wherein the ionic strength of the buffer solution for elution is in the range of 0.05 to 0.8.

5. A process for the production of a purified S-sulfonated gammaglobulin which comprises treating an S-sulfonated gammaglobulin with a cation exchanger in a buffer solution for development having a pH level of 4 to 6.5 and an ionic strength of 0.01 to 0.1 and thereby absorbing single molecular S-sulfonated gammaglobulin onto the cation exchanger, and then eluting the single molecular S-sulfonated gammaglobulin with a buffer solution for elution.

6. A process according to claim 5, wherein the cation exchanger is a member selected from the group consisting of agarose gel introduced with a cationic substituent, dextran gel introduced with a cationic substituent, cellulose gel introduced with a cationic substituent, polyvinyl gel introduced with a cationic substituent, and amylose gel introduced with a cationic substituent, said cationic substituent being a member selected from the group consisting of carboxymethyl, sulfopropyl and sulfoethyl.

7. A process according to any one of claim 5, 8 or 9, wherein a buffer solution having a pH level of 6 to 9 and an ionic strength of higher than that of the buffer solution for development is used as the buffer solution for elution.

8. A process according to claim 7, wherein the ionic strength of the buffer solution for development is in the range of 0.05 to 0.8.

9. A process for separating single molecules from aggregated molecules of S-sulfonated gammaglobulin which comprises preferentially absorbing the said single molecules on an ion exchanger from a buffered solution having a pH which is compatable with the ion exchanger and eluting the ion exchanger to remove the absorbed gamma globulin.

* * * * *